United States Patent [19]

Burruano et al.

[11] Patent Number: 6,110,502

[45] Date of Patent: Aug. 29, 2000

[54] METHOD FOR PRODUCING WATER DISPERSIBLE STEROL FORMULATIONS

[75] Inventors: Brid Burruano, King of Prussia; Richard D. Bruce, Rydal; Michael R. Hoy, Sellersville, all of Pa.

[73] Assignee: McNeil-PPC, Inc., Skillman, N.J.

[21] Appl. No.: 09/025,952

[22] Filed: Feb. 19, 1998

[51] Int. Cl.$^7$ ............ A61K 9/00; A61K 47/00; A61K 9/20; A61K 9/14; A61K 9/50

[52] U.S. Cl. ............ 424/499; 424/400; 424/439; 424/464; 424/489; 424/500; 424/501

[58] Field of Search ............ 424/489, 502, 424/450, 195.1, 400, 464, 439, 499, 500, 501; 514/178, 937

[56] References Cited

U.S. PATENT DOCUMENTS

| | | |
|---|---|---|
| 3,004,043 | 10/1961 | Stern . |
| 3,085,939 | 4/1963 | Wruble et al. . |
| 3,865,939 | 2/1975 | Jandacek . |
| 3,881,005 | 4/1975 | Thakker et al. ............ 424/238 |
| 4,005,196 | 1/1977 | Jandacek et al. . |
| 4,195,084 | 3/1980 | Ong ............ 424/238 |
| 4,423,041 | 12/1983 | Clum et al. . |
| 5,219,733 | 6/1993 | Myojo et al. . |
| 5,244,887 | 9/1993 | Straub . |
| 5,270,041 | 12/1993 | Eugster et al. ............ 424/195.1 |
| 5,492,714 | 2/1996 | Guskey et al. . |
| 5,502,045 | 3/1996 | Miettinen et al. . |
| 5,578,334 | 11/1996 | Sundram et al. . |
| 5,629,316 | 5/1997 | Kurihara et al. . |
| 5,698,527 | 12/1997 | Kim . |
| 5,932,562 | 8/1999 | Ostlund, Jr. ............ 514/78 |

FOREIGN PATENT DOCUMENTS

| | | |
|---|---|---|
| 0 057 075 B1 | 6/1984 | European Pat. Off. . |
| 0 053 415 B1 | 9/1985 | European Pat. Off. . |
| 0 289 636 A1 | 9/1988 | European Pat. Off. . |
| 0 357 967 | 3/1990 | European Pat. Off. ...... A61K 37/575 |
| 1284814 | 9/1972 | United Kingdom . |
| 92/19640 | 12/1992 | WIPO . |
| 93/10033 | 4/1996 | WIPO . |
| 96/38047 | 5/1996 | WIPO . |
| 98/06714 | 2/1998 | WIPO . |

OTHER PUBLICATIONS

Sjostrom, B. et al: "A Method for the Preparation of Submicron Particles of Sparingly Water–soluble Drugs by Precipitation in Oil–in–Water Emulsions II: Influence of the Emulsifier, the Solvent, and the Drug Substance", Journal of Pharmacuetical Sciences, vol. 82, No. 6, Jun. 1, 1993, pp. 584–589.

T. Heinemann et al., "Mechanisms of Action of Plant Sterols on Inhibition of Cholesterol Absorption," Eur. J. Clin. Pharmacol (1991) 40 [Suppl 1]: pp. 59–63.

*Primary Examiner*—Thurman K. Page
*Assistant Examiner*—Todd D Ware
*Attorney, Agent, or Firm*—Joseph F. Leightner

[57] ABSTRACT

A method for preparing β-sitosterol is disclosed which provides the sterol in a readily consumable form. The method includes the spray drying of the β-sitosterol in a mixed micelle formulation. The product is provided in a convenient form that can be provided to food or drinks or incorporated into solid and suspension dosage forms.

17 Claims, No Drawings

METHOD FOR PRODUCING WATER DISPERSIBLE STEROL FORMULATIONS

BACKGROUND OF THE INVENTION

The present invention relates to a method of producing spray dried aqueous-dispersible sterol formulations, in particular a method for producing dispersible β-sitosterol via a spray drying process.

As disclosed in U.S. Pat. Nos. 5,502,045, 5,578,334 and 5,244,877, it is known that consumption of β-sitosterol is known to reduce cholesterol levels in the blood stream. Presently, β-sitosterol is incorporated in foods as an ingredient of the food while it is being prepared. While this is effective in producing foods with beneficial effects, the consumer is limited to those foods in which the manufacturers have decided to incorporate the β-sitosterol.

It would be highly desirable to provide β-sitosterol in a convenient ready to consume form in which consumers could apply to food just prior to eating. A particularly convenient form would be a single serving packet of β-sitosterol similar to those that are currently available for artificial sweeteners. The difficulty in providing β-sitosterol in this form is that it is difficult to separate the active ingredient from other sterols, namely stigmasterol, campesterol and the like.

Attempts at solving this problem are disclosed in U.S. Pat. Nos. 3,881,005 and 4,195,084 in which water dispersible sitosterols are formed by mixing with an excipient and a suitable surfactant. While this disclosure produces a water dispersible sitosterol, it would be highly advantageous to improve the water dispersibility of the β-sitosterol, since this is believed to be the more effective form as a cholesterol lowering agent.

SUMMARY OF THE INVENTION

A primary object of the present invention is to provide a method for preparing a stable spray dried powder matrix that has self-emulsifying character upon addition to aqueous media. The process embodied in this invention involves:

incorporating β-sitosterol into an aqueous suspension by use of a mixed surfactant system comprising a monofunctional and a polyfunctional surfactant; and drying the sterol suspension thereby providing a water-dispersible β-sitosterol; wherein the above process is performed in the absence of deaeration and homogenization steps.

DETAILED DESCRIPTION OF THE INVENTION

β-sitosterols are typically derived from wood or agricultural sources, such as soy based mixtures. In addition to β-sitosterol, as used throughout this application, β-sitosterol is also understood to include the esters of β-sitosterols, as well the stanol forms which are the oxidized form of the sterols. These derivatives are well known in the art and include patents U.S. Pat Nos. 5,244,887; 5,502,045 and 5,698,527. The β-sitosterols produced by the present invention are water dispersible. As used herein, water dispersible is understood to mean that when the β-sitosterol spray dried formulation is placed in water, at least 200 mg formula/mil water will disperse with mild agitation. Those with skill in the art will appreciate that ordinarily β-sitosterols are hydrophobic materials, and upon the addition of the β-sitosterol to water, the β-sitosterol will float on top of the water and will not become dispersed.

In order to be most effective when ingested, the particle size of the β-sitosterol should be in the range of from 10 to 40 microns. More preferably the particle size should from about 20 to 35 microns. Any grinding technique known in the art may be used to grind the β-sitosterol. Suitable methods include pulverizing, rotary hammermill, air milling and the like of which air milling is most preferred. Smaller particles sizes are preferred in that the resulting β-sitosterol product is more readily exposed to bile salts in the digestive tract. The handling properties of the smaller particle size product are less desirable, resulting in higher angle of rupture, higher angle of repose and compressibility. The handling of the water-dispersible β-sitosterol product can be improved with increased particle size; however, this is believed to be detrimental to the efficacy of the β-sitosterol in reducing serum cholesterol.

In order to form the water dispersible β-sitosterols appropriate surfactants are required. The present invention employs a dual surfactant system. One surfactant in the system is monofunctional, while the second surfactant is polyfunctional. The monofunctional surfactants tend to be more hydrophobic, whereas the polyfunctional surfactants tend to be hydrophilic. The two-surfactant system employed in this invention creates a mixed micelle system that results in the water-dispersible product. As used herein monofunctional is defined as the ability of the surfactant to bond to the β-sitosterol. The polyfunctional surfactant has the ability to bond to the β-sitosterol as well as to the other surfactant.

Useful surfactants in the practice of the present invention include polyglycerol esters, polysorbates, mono and diglycerides of fatty acids, propylene glycol esters, sucrose fatty acid esters and polyoxyethylene derivatives of sorbitan fatty acid esters. These surfactants are well known in the art and are commercially available.

Suitable polyglycerol esters include triglyceryl monostearate, hexaglyceryl distearate, hexaglyceryl monopalimate, hexaglyceryl dipalmitate, decaglyceryl distearate, decaglyceryl monoleate, decaglyceryl dioleate, decaglycerol monopalmitate, decaglycerol dipalmitate, decaglyceryl monostearate, octaglycerol monoleate, octaglycerol monostearate and decaglycerol monocaprylate.

Other useful surfactants include polysorbates made from the reaction product of monoglycerides or sorbitan esters with ethylene oxides. Examples of useful polysorbates include polyoxyethylene 20 mono- and diglycerides of saturated fatty acids, polyoxyethylene 4 sorbitan monostearate, polyoxyethylene 20 sorbitan tristearate, polyoxyethylene 20 sorbitan monooleate, polyoxyethylene 5 sorbitan monooleate, polyoxyethylene 20, sorbitan trioleate, sorbitan monopalmitate, sorbitan monolaurate, propylene glycol monolaurate, glycerol monostearate, diglycerol monostearate, glycerol lactyl-palmitate.

Other suitable surfactants include, with HLB values provided in brackets, [ ], include decaglycerol monolaurate[15.5]; decaglycerol distearate [10.5]; decaglycerol dioleate [10.5]; decaglycerol dipalmitate [11.0]; decaglycerol monostearate [13.0]; decaglycerol monooleate [13.5]; hexaglycerol monostearate [12.0]; hexaglycerol monooleate [10.5]; hexaglycerol monoshortening [12.0]; polyoxyethylene (20) sorbitan monolaurate [16.7]; polyoxyethylene (4) sorbitan monolaurate [13.3]; polyoxyethylene (20) sorbitan monopalmitate [15.6]; polyoxyethylene (20) sorbitan monostearate [14.9]; polyoxyethylene (20) sorbitan tristearate [10.5]; polyoxyethylene (20) sorbitan monooleate [15.0]; polyoxyethylene (5) sorbitan monooleate [10.0]; polyoxyethylene (20) sorbitan trioleate [11.0]. As is appreciated by those with skill in the art, the HLB value for a surfactant is an expression of its Hydrophile-Lipophile balance, i.e., the balance of the size and strength of the hydrophilic (polar) and lipophilic (non-polar) groups of the surfactant.

Lactic acid derivatives include sodium stearoyl lactylate and calcium stearoyl lactylate.

The level of monofunctional surfactant is typically from about 1 to about 10 weight percent based upon the final dried weight of the β-sitosterol product, preferably from about 1.5 to about 4, and most preferably about 2.0 to about 2.5 weight percent. The level of polyfunctional surfactant is typically from about 0.5 to about 10 weight percent based upon the final dried weight of the β-sitosterol product, preferably from about 2 to about 4, and most preferably about 2.0 to about 2.5 weight percent. TWEEN 40 is the preferred monfunctional surfactant and SPAN 80 is the preferred polyfunctional surfactant. Suitable ratios of mofunctional/polyfunctional surfactants which form the mixed micelle include from about 1:6 to about 1.5:1, preferably from about 1:4 to about 1.3:1, most preferably about 1:1 ratio. The level of surfactant employed ranges from about 0.5 to about 8 percent by weight total surfactant system, preferably 1 to about 6, most preferably from about 3 to about 4 percent by weight.

In a preferred embodiment, in addition to the surfactant, other excipients, tableting aids etc. are added to the formulation as the suspension is formed, prior to the spray drying process. This conveniently incorporates tableting aids and other necessary ingredients thereby eliminating or reducing unit-manufacturing steps. If desired, ingredients can also be added to the β-sitosterol after spray drying.

For example, lubricants, glidants, carriers, sweeteners, disintegrants, preservatives and other ingredients may be added to the suspension in the amount of from about 5 to about 40 weight percent, typically from about 10 to about 30 percent and most preferably to about 20 to about 25 percent. Suitable ingredients include binders are acacia mucilage, starch mucilage pregelatinised starch, sodium alignate, hydroxypropylmethyl cellulose (HPMC), starch paste, polyvinylpyrrolidone, carboxymethylcellulose, dextrin, ethyl cellulose, polyethylene glycol, guar gum, zein, hydroxyethyl cellulose, hydroxypropyl cellulose, methyl cellulose, polymethacrylates, and carboxymethylcellulose.

Disintegrating agents include microcystalline cellulose (e.g. Avicel R), sodium carboxymethyl cellulose (e.g. Nymcel R), modified cellulose gum (e.g. Ac-Di-Sol R), crosslinked providone, alginic acid and alginates, pregelatinised starch, sodium starch glycollate (e.g. Explotab R, Primojel R), modified corn starch (e.g. starch 1500R), starch (e.g. potato/maize starch), and ion exchange resin such as polacrin potassium (e.g. Amberlite IRP-88).

Examples of water-soluble fillers are: soluble lactose, compressible sugar, confectioners sugar, dextrose, mannitol, sodium chloride, sorbitol, xylitol. Examples of water-insoluble fillers are: calcium carbonate, magnesium carbonate, calcium phosphate (e.g. di and tri basic calcium phosphate), calcium sulphate, kaolin, microcystalline cellulose, powdered cellulose, pregelatinized starch, barium sulphate, magnesium trisilcate, aluminum hydroxide.

Generally lubricants are used in as low an amount as possible. Examples of lubricants include: stearates (e.g. magnesium or calcium stearate), talc, polyethylene glycol, liquid paraffin, sodium lauryl sulphate, magnesium lauryl sulphate, colloidal silicone dioxide, palmitostearate, stearic acid, zinc stearate, hydrogenated vegetable oil.

Glidants including talc, starch, magnesium stearate, silica derivatives, such as colloidal silica (e.g. AEROSIL) pyrogenic silica, hydrated sodium silicoaluminate, colloidal silicon dioxide.

Flavouring agents including orange, cherry, and strawberry, raspberry, grape and passion fruit.

Sweetening agents, include for example, sodium saccharin, aspartame, confectioners sugar, sorbitol, xylitol and mixtures thereof.

The β-sitosterol and the other ingredients in the suspension should be uniformly mixed. Preferably the suspension is mixed by agitation, preferably through the use of a high-speed mixer. The particle size of the micelles in the suspension formed are from about 50 to about 400 microns, preferably from about 100 to about 300 microns and most preferably from about 150 to about 250 microns in size. The size of the micelles formed in the suspension may be measured through the use of a Turbimeter. The greater turbidity, the larger the micelle formation. It is expected that greater turbidty, i.e., larger micelles provides a more effective form of the β-sitosterol for reducing cholesterol when consumed. Preferred turbidity levels are greater than about 2000, preferably greater than 2500 and most preferably greater than 3000 Nepthialic Turbidity Units (NTU). As used herein turbidity is understood to be the same as defined by the United States Pharmacopeia, the light scattering effect of suspended particles and turbidity as the measure of the decrease in the incident beam intensity per unit length of a given suspension. The range of turbidty values is from 0 to 20,000 NTU. As a point of reference the turbidity of water is zero. The turbidity of the samples was measured at room temperature.

After the suspension with the proper particle size is formed the suspension is dried. Suitable drying methods include freeze drying, rotary, vacuum and spray drying, of which spray drying is preferred. The final moisture content of the dried β-sitosterol is preferably less than 1% by weight water. Lower moisture content generally provides improved flow characteristics.

When spray drying the suspension, it is preferable that the inlet temperature is from about 100 to 120° C., preferably from about 105 to about 115° C. and most preferably from 107 to about 112° C. The outlet temperature of the spray dryer is between about 65 and 85° C. and most preferably from about 73 to about 80° C.

The spray dried water-dispersible β-sitosterol product is then recovered. The resulting water-dispersible β-sitosterol is comprised of from greater than 50 percent by weight sterol, greater than 4 and preferable from about 5 to about 10 weight percent surfactant. In a highly preferred embodiment the β-sitosterol also includes about 5 percent starch and about 5 percent silicon dioxide.

After the β-sitosterol is removed from the dryer it is packaged in any suitable size as may be required. The form in which the β-sitosterol is consumed varies depending on the preference of the consumer. Suitable forms include tablets, chewable dosages, in the preparation of food and beverages as well as applied to prepared beverages and foodstuffs. In a preferred embodiment, the β-sitosterol may be packaged in single serving size packets containing from about 5 to about 50 grams per packet.

The present invention provides advantages over previous disclosures that provide water-dispersible β-sitosterols in that several costly and time consuming process steps are eliminated. Prior disclosures required both a homogenization and deaeration step in order to produce the water-dispersible β-sitosterol. The present invention provides the water-dispersible β-sitosterol through the use of the selection of advantageous combinations of surfactants. The invention will now be illustrated by, but is not intended to be limited to, the following examples. In the examples the starch was ground to a particle size of approximately 10 microns. In these examples it is understood that unless noted otherwise, all parts are weight percent.

The following raw materials are available from the following suppliers.

CAB O SIL colloidal silicon dioxide, Degussa Corp.

AEROSIL A200 colloidal silicon dioxide, Cabot Corp.

EM Compress dibasic calcium phosphate dihydrate, Edward Mendall Compress Co., Inc.

M100 maltrodextrin (dextrose equivalent of about 10) Grain Process Corp.

Pluronic L-44 a polyethylene-propylene glycol copolymer, BASF Corp.

SPAN 80 sorbitan monooleate, ICI Americas, Inc.

starch—Starch NF-, National Starch and Chemicals Inc.

Sterols—Generol 122N available from Henkel Company, Ambler, Pa.

TWEEN 40 polyoxyethylene 20 sorbitan monopalmitate, ICI Americas Inc.

TWEEN 60 polyoxyethylene 20 sorbitan monostearate, ICI Americas Inc.

EXAMPLE 1

This example discloses a formulation for spray dried material containing approx. 75% sterols (based on dry weight). Any polyoxyethylene sorbitan fatty acid ester can be incorporated in the place of TWEEN 60.

| Component: | Amount (gm): |
|---|---|
| TWEEN 60 | 30 |
| Maltodextrin - Maltrin M100 | 240 |
| Aerosil A200 | 22 |
| Starch NF | 75 |
| Phytosterols | 1,120 |
| Water | 10,000 |

The sample is prepared as follows: the TWEEN 60 and 500 gm water of water was added and the mixture was stirred on a hot plate set at 60° C. until uniform. The solution was transferred into a larger container, rinsing with water. An additional remaining 9,500 gm of water was added. The starch, Maltrin M100, Aerosil 200 and the sterols were weighed out and added to the solution. The resulting solution was mixed with high shear mixer for approximately 1 hour. The suspension was spray dried immediately afterwards.

The turbidity of 100 mg of the resulting spray dry powder in 25 ml of water was approximately 300 NTU.

EXAMPLE 2

The following example outlines a spray dry formulation containing approx. 75% sterols (based on dry weight).

| Component: | Amount (gm): |
|---|---|
| Docusate Sodium | 40 |
| Maltodextrin - Maltrin M100 | 240 |
| Aerosil A200 | 22 |
| Starch NF | 75 |
| Phytosterols | 1,120 |
| Water | 10,000 |

The sample is prepared as follows: the docusate sodium was weighed into a beaker, 500 gm water of water was added and the mixture was stirred on a hot plate set at 60° C. until uniform. The solution was transferred into a larger container, rinsing with water. An additional remaining 9,500 gm of water was added. The starch, Maltrin M100, Aerosil 200 and the sterols were weighed out and added to the solution. The resulting solution was mixed with high shear mixer for approximately 1 hour. The suspension was spray dried immediately afterwards.

The turbidity of the 100 mg of the resulting spray dried powder in 25 ml of water was approximately 2400 NTU.

EXAMPLE 3

The following example outlines a spray dry formulation containing approx. 75% sterols (based on dry weight). Any poloxamer can be incorporated in place of Pluronic L-44.

| Component: | Amount (gm): |
|---|---|
| Pluronic L-44 | 80 |
| Maltodextrin - Maltrin M100 | 240 |
| Aerosil A200 | 22 |
| Starch NF | 75 |
| Phytosterols | 1,120 |
| Water | 10,000 |

The sample is prepared as follows: the Pluronic L-44 was weighed into a beaker, 500 gm water of water was added and the mixture was stirred on a hot plate set at 60° C. until uniform. The solution was transferred into a larger container, rinsing with water. An additional remaining 9,500 gm of water was added. The starch, Maltrin M100, Aerosil 200 and the sterols were weighed out and added to the solution. The resulting solution was mixed with high shear mixer for approximately 1 hour. The suspension was spray dried immediately afterwards.

The Turbidity of the 100 mg of the resulting spray dried powder in 25 ml of water was approximately 2600 NTU.

EXAMPLE 4

| Component: | Amount (gm): |
|---|---|
| TWEEN 40 | 40 |
| SPAN 80 | 40 |
| Maltodextrin - Maltrin M100 | 240 |
| Aerosil A200 | 22 |
| Starch NF | 75 |
| Phytosterols | 1,120 |
| Water | 10,000 |

The sample was prepared as follows: the Tween and Span were weighed into a beaker, 500 gm water of water was added and the mixture was stirred on a hot plate set at 60° C. until uniform. The solution was transferred into a larger container, rinsing with water. An additional remaining 9,500 gm of water was added. The starch, Maltrin M100, Aerosil 200 and the sterols were weighed out and added to the solution. The resulting solution was mixed with high shear mixer for approximately 1 hour. The suspension was spray dried immediately afterwards.

The turbidity of the 100 mg of the resulting spray dried powder in 25 ml of water was approximately 3500 NTU.

What is claimed is:

1. A process for preparing water-dispersible β-sitosterol comprising:

providing an aqueous stream admixing to the aqueous stream from about 2 to about 2.5 weight percent of a monofunctional surfactant and from about 2 to about 2.5 weight percent of a polyfunctional surfactant to form a water surfactant mixture;

admixing β-sitosterol to the water surfactant mixture to form a β-sitosterol suspension;

drying the β-sitosterol suspension to recover a water-dispersible β-sitosterol;

wherein the above process is performed in the absence of deaeration and homogenization steps.

2. The process of claim 1 wherein drying is performed by spray drying.

3. The process of claim 1 wherein the β-sitosterol suspension has a turbidity of greater than 2000 NTU.

4. The process of claim 1 wherein the spray drying step is conducted at outlet temperature of from about 65 to about 85° C.

5. The process of claim 1 wherein the weight ratio of the monofunctional surfactant to the polyfunctional surfactant is about 1:1.

6. The process of claim 1 wherein the β-sitosterol suspension is formed through the use of a high-speed mixer.

7. The process of claim 1 wherein the β-sitosterol is ground.

8. The process of claim 10 wherein the β-sitosterol is ground prior to the formation of the β-sitosterol suspension.

9. The product provided by the process of claim 1.

10. The product of claim 9 provided in a single serving container providing from about 5 to about 50 grams of water-dispersible β-sitosterol.

11. A process for preparing water-dispersible β-sitosterol comprising:

providing an aqueous stream admixing to the aqueous stream from about 2 to about 2.5 weight percent polyoxyethylene sorbitan monopalmitate and from about 2 to about 2.5 weight percent sorbitan monooleate to form a water surfactant mixture;

admixing β-sitosterol to the water surfactant mixture to form a β-sitosterol suspension;

drying the β-sitosterol suspension to recover a water-dispersible β-sitosterol;

wherein the above process is performed in the absence of deaeration and homogenization steps.

12. The process of claim 11 wherein drying is performed by spray drying.

13. The process of claim 11 wherein the β-sitosterol suspension has a turbidity of greater than about 3000 NTU.

14. The process of claim 11 wherein the weight ratio of the polyoxyethylene sorbitan monopalmitate to the polyoxyethylene sorbitan monooleate surfactant is about 1:1.

15. The process of claim 11 wherein the β-sitosterol suspension is formed through the use of a high-speed mixer.

16. The product provided by the process of claim 11.

17. The product of claim 16 provided in a single serving container providing from about 5 to about 50 grams of water-dispersible β-sitosterol.

* * * * *